United States Patent [19]

Flatland et al.

[11] Patent Number: 5,752,938
[45] Date of Patent: May 19, 1998

[54] SEAL FOR SURGICAL INSTRUMENTS

[75] Inventors: Martin L. Flatland; Jeffrey W. Zerfas, both of Kalamazoo, Mich.

[73] Assignee: Richard-Allan Medical Industries, Inc., Richland, Mich.

[21] Appl. No.: 486,146

[22] Filed: Jun. 7, 1995

Related U.S. Application Data

[63] Continuation-in-part of Ser. No. 304,507, Sep. 12, 1994, abandoned.

[51] Int. Cl.⁶ .................................................. A61M 39/22
[52] U.S. Cl. .......................................... 604/167; 604/256
[58] Field of Search ................................. 604/167, 256, 604/247; 137/846, 849

[56] References Cited

U.S. PATENT DOCUMENTS

| | | | |
|---|---|---|---|
| 2,822,819 | 2/1958 | Geeraert | 137/849 |
| 2,944,580 | 7/1960 | Nece | 137/846 |
| 3,047,013 | 7/1962 | Baumbach | 137/849 |
| 3,113,586 | 12/1963 | Edmark, Jr. | 137/846 |
| 3,517,622 | 6/1970 | Smith | 137/846 |
| 3,853,127 | 12/1974 | Spademan | 128/214.4 |
| 3,861,416 | 1/1975 | Wichterle | 137/849 |
| 3,994,287 | 11/1976 | Turp et al. | 128/6 |
| 4,222,126 | 9/1980 | Boretos et al. | 137/846 |
| 4,291,420 | 9/1981 | Reul | 137/846 |
| 4,364,127 | 12/1982 | Pierce et al. | 137/849 |
| 4,430,081 | 2/1984 | Timmermans | 604/256 |
| 4,524,805 | 6/1985 | Hoffman | 137/846 |
| 4,607,663 | 8/1986 | Raftis et al. | 137/846 |
| 4,673,393 | 6/1987 | Suzuki et al. | 604/167 |
| 4,723,550 | 2/1988 | Bales et al. | 128/344 |
| 4,813,938 | 3/1989 | Raulerson | 604/167 |
| 4,842,591 | 6/1989 | Luther | 604/283 |
| 4,857,062 | 8/1989 | Russell | 604/256 |
| 4,909,798 | 3/1990 | Fleischhacker et al. | 604/256 |
| 4,960,412 | 10/1990 | Fink | 604/167 |
| 4,966,588 | 10/1990 | Rayman et al. | 604/165 |
| 5,000,745 | 3/1991 | Guest et al. | 604/256 |
| 5,009,391 | 4/1991 | Steigerwald | 251/149.1 |
| 5,053,014 | 10/1991 | Van Heugten | 604/167 |
| 5,104,383 | 4/1992 | Shichman | 604/167 |
| 5,180,373 | 1/1993 | Green et al. | 607/167 |
| 5,197,955 | 3/1993 | Stephens et al. | 604/167 |
| 5,209,737 | 5/1993 | Ritchart et al. | 604/167 |
| 5,242,412 | 9/1993 | Blake, III | 604/167 |
| 5,269,763 | 12/1993 | Boehmer et al. | 604/167 |
| 5,304,143 | 4/1994 | Green et al. | 604/167 |
| 5,330,437 | 7/1994 | Durman | 604/167 |
| 5,334,164 | 8/1994 | Guy et al. | 604/248 |
| 5,342,315 | 8/1994 | Rowe et al. | 604/167 |
| 5,350,364 | 9/1994 | Stephens et al. | 604/167 |
| 5,407,433 | 4/1995 | Loomas | 604/167 |

OTHER PUBLICATIONS

Page from Auto Suture Catalog (1994).
Pages from Applied Laproscopy Catalog (1992).

*Primary Examiner*—Paul I. Hirsch
*Attorney, Agent, or Firm*—Howard & Howard

[57] ABSTRACT

An adaptable seal for use in a trocar or trocar converter is provided. The seal comprises a membrane having a radially proximal edge and a radially distal edge, at least one lobe terminating at said band, and preferably a band located at the radially proximal edge. The seal is thus able to adaptably receive surgical instruments of various diameters. The seal may further comprise means for forming a fluid-tight seal between the upper surface and the lower surface of the seal when an elongated object is received through an aperture in the seal, and at least one trough or wall. A seal according to the present invention is able to accommodate radial movement of the surgical instrument within the cannula of a trocar. A trocar and a trocar converter also fall within the purview of the present invention.

34 Claims, 11 Drawing Sheets

SEAL FOR SURGICAL INSTRUMENTS

This is a continuation-in-part of application Ser. No. 08/304,507 filed on Sep. 12, 1994 now abandoned.

TECHNICAL FIELD OF THE INVENTION

The present invention is directed towards an adaptable seal that may sealably receive elongated objects of various diameters. Specifically, the present invention is directed towards an adaptable seal for use in a trocar or trocar converter.

BACKGROUND OF THE INVENTION

Medical science has long sought ways to minimize the dangers and trauma inherent in invasive surgical procedures. To this end, surgical techniques and instruments have been developed which, among other things, reduce the size of the incisions required to perform various surgical procedures. These techniques and instruments have been remarkably successful. Indeed, surgical procedures which only a few years ago would require an incision of several inches in length are today being performed through incisions which are less than one inch in length.

Trocars are one type of surgical instrument which have significantly contributed to these advances. In general, trocars are sharp, pointed surgical instruments which can be used to create and maintain small, hole-like incisions in a body cavity. Surgical instruments, including miniaturized optical devices, can be inserted through these trocars and manipulated to perform surgical procedures within the body cavity. Thus, by enabling the creation and maintenance of small working channels within a patient's body wall, conventional trocars have greatly contributed to the reduction in size of the incisions required to perform surgical procedures and reduced the related complications.

Trocars generally include an obturator and a cannula. An obturator is a sharp, nail-like structure for penetrating a body wall to create a working channel into the body cavity. A cannula is a tube-like structure which can be inserted into the incision made by the obturator to maintain the working channel even after the obturator is removed. In the typical scenario, the obturator and cannula are assembled into a single unit (i.e., by inserting the obturator into the cannula) and then used to puncture the body wall. The obturator can then be carefully withdrawn from the cannula without removing the cannula from the body wall. An example of a trocar is disclosed in U.S. patent application Ser. No. 08/189,318 filed Jan. 31, 1994 entitled "Trocar Assembly" which is assigned to the assignee of this application and is herein incorporated by reference in its entirety.

Surgical instruments can be inserted through this cannula to perform an entire surgical procedure within the body cavity as mentioned above. These surgical instruments may comprise a cylindrical shaft, an operating mechanism, such as a pair of scissors, an actuator, such as a handle, and means for actuating the operating end, such as a drive shaft within the cylindrical shaft. Alternately, the instrument can be an optical device that comprises one or more fiber optic cables within a cylindrical shaft.

Ideally, the surgical instruments used in such procedures should be as small as possible, in order to minimize the possibility of trauma. Surgical instruments have been developed that have an effective diameter of 5 mm; i.e., having a cylindrical shaft with a diameter of approximately 5 mm. These instruments tend to have a simple construction.

Other, more complex surgical instruments are not able to fit within such a small shaft, and require a larger effective diameter. Generally, surgical instruments having an effective diameter of up to about 14 mm may be used in such surgical procedures. A surgeon may often find it desirable to insert and remove several surgical instruments through one cannula in a single surgical procedure.

During such surgical procedures, a fluid-tight seal must e maintained between the outside environment and the inside of the patient. The patient is insufflated with an insufflation gas, typically carbon dioxide, and thus the fluid-tight seal is used to prevent the insufflation gas, blood and other fluids from escaping from the patient's body. The seal further acts to prevent contamination of the patient's body by the outside environment. Without such a fluid-tight seal, many of the attendant advantages of such surgical procedures would be lost. At present, trocars are made with conventional seals, which consist of a washer-shaped ring of a flexible material, such as an elastomer, sized so as to accommodate the cylindrical shaft of the surgical instrument.

Because instruments of varying diameters are often inserted into the same cannula during a single surgical procedure, maintenance of a fluid-tight seal between the inside of the patient and the outside environment is impossible with a conventional seal when the seal is not sized so as to receive the instrument. In order to allow the use of multiple surgical instruments of varying sizes, the surgeon typically begins with a trocar having a cannula large enough to accommodate the largest surgical instrument needed for the procedure. To use a smaller surgical instrument, the surgeon inserts a trocar converter onto the top of the trocar. Typically, a trocar converter has a short tubular channel that coincides with that of the cannula. The trocar converter also contains a seal able to sealably receive an instrument having a smaller effective diameter than the diameter of the cannula. An example of a converter is disclosed in U.S. patent application Ser. No. 08/189,318.

When the surgeon desires to change instruments frequently, the use of trocar converters can make the surgical procedure much more complicated. For example, the surgeon may desire to use several different instruments having diameters of, for example, 5 mm, 7 mm, 10 mm, and 12 mm, all within a matter of a few minutes. A trocar able to accommodate a 12 mm instrument and three separate converters would be required for such a procedure. During surgery, these converters may become lost or disorganized, and valuable time may be lost in exchanging the converters.

An additional complication arises from the practices of some manufacturers of surgical instruments. A surgical instrument may bear the nominal notation "10 mm", yet have a true diameter that is more or less than 10 mm. Thus, a 10 mm surgical instrument sold by one manufacturer may have an actual size that is slightly different from a 10 mm trocar or trocar converter sold by another manufacturer. If the products vary in size, a conventional seal may not provide a fluid-tight seal, and the products will thus be incompatible. Of course, the surgeon may wish to use a variety of surgical instruments from a number of different manufacturers. This may prove to exceedingly difficult, especially where the surgical procedure involves a large number of instruments.

An additional problem encountered with the use of conventional seals is that of radial movement of surgical instruments. When a surgical instrument having a small diameter is inserted into a trocar having a large diameter, the surgical instrument often does not travel straight into the cannula, but instead may move in a radial direction within the cannula. Radial movement is exacerbated as the difference in the diameter of the surgical instrument and the diameter of the trocar increases. Conventional seals are not designed to accommodate such radial movement, and often must stretch awkwardly in such situations, increasing the risk that the seal will rupture or leak.

Ideally, the surgeon should be able to use one trocar or trocar converter throughout the surgical procedure, and should be able to insert and remove surgical instruments of all sizes without having to exchange converters. Moreover, the surgeon should be able to use surgical instruments from a number of different manufacturers, without the worry of incompatibility. Further, the surgeon should not have to worry about the effect of radial movement of the surgical instrument on the integrity of the fluid-tight seal around the surgical instrument. Conventional seals do not allow for such properties. In addition, although one adaptable seal is known in the prior art, this seal requires a complicated mechanism to adjust to surgical instruments of various diameters and would thus be expensive to manufacture. Accordingly, the present invention seeks to provide an adaptable seal that is simple in construction and that overcomes the shortcoming of conventional seals.

BRIEF SUMMARY OF THE INVENTION

The present invention provides an adaptable seal for sealably receiving elongated objects of various diameters, said adaptable seal comprising a membrane having a radially proximal edge and a radially distal edge, at least one lobe in the membrane which terminates at the radially proximal edge, wherein at least a portion of the radially proximal edge defines an adjustable aperture for receiving elongated objects. Preferably, the seal has a band at the radially proximal edge, wherein the band defines an adjustable aperture for sealably receiving elongated objects. Further, the present invention provides a seal for sealably receiving elongated objects, the seal comprising a membrane having an upper surface and a lower surface, a radially proximal edge and a radially distal edge, an aperture, and at least one trough located between the radially distal edge and the radially proximal edge, wherein the seal forms a fluid-tight seal between the upper surface and lower surface when an elongated object is received through the aperture. The present invention further provides a seal for sealably receiving elongated objects, the seal comprising a membrane having an upper surface and a lower surface, a radially proximal edge and a radially distal edge, an aperture, and a wall located at the radially distal edge. A trocar and a trocar converter incorporating a seal according to the present invention also fall within the scope of the present invention.

DETAILED DESCRIPTION OF THE PREFERRED EMBODIMENTS

With reference to FIGS. 1, 2, 3, and 4, seal 30 comprises membrane 32 having radially proximal circumferential edge 34 and radially distal circumferential edge 36. Membrane 32 contains lobes 44 which terminate at radially proximal circumferential edge 34. The lobes 44 and radially proximal circumferential edge 34 are shaped so as to allow insertion of surgical instruments. Seal 30 preferably further comprises a band 48 attached to membrane 32 at radially proximal circumferential edge 34. Band 48 defines an adjustable aperture 38 which may sealably receive surgical instruments of varying diameters.

Figures 1, 2, 3, 4:
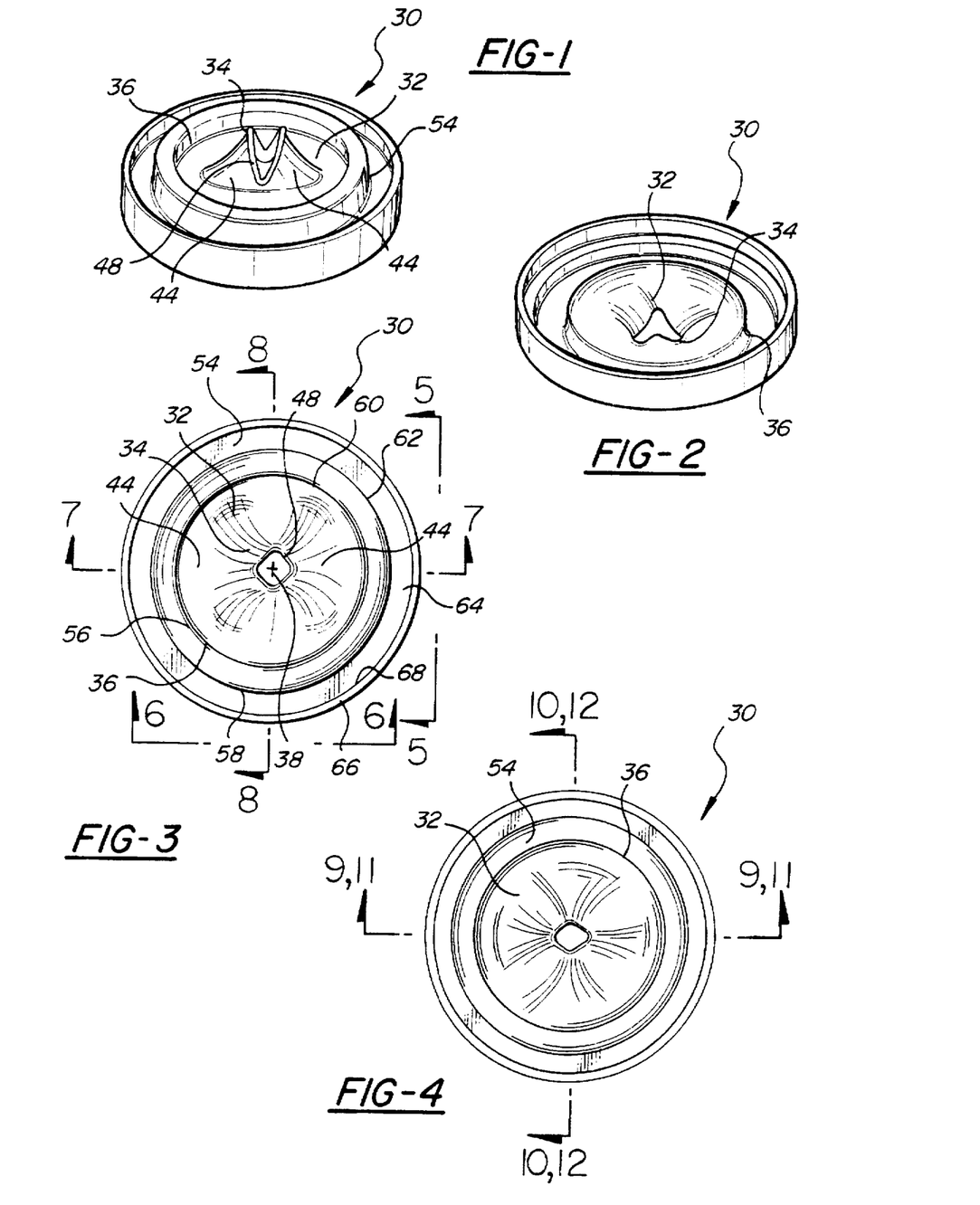
FIG. 1 is a bottom perspective view of an embodiment of the adaptable seal of the present invention having two lobes and a cone-shaped membrane.
FIG. 2 is a top perspective view of the adaptable seal illustrated in FIG. 1.
FIG. 3 is a bottom plan view of the adaptable seal illustrated in FIG. 1.
FIG. 4 is a top plan view of the adaptable seal illustrated in FIG. 1.
Figure 5:
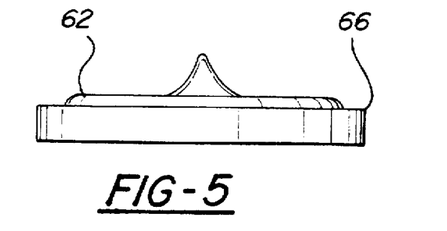
FIG. 5 is a side view of the adaptable seal illustrated in FIG. 1 taken along line 5—5 in FIG. 3.
Figures 19, 20, 21, 22:
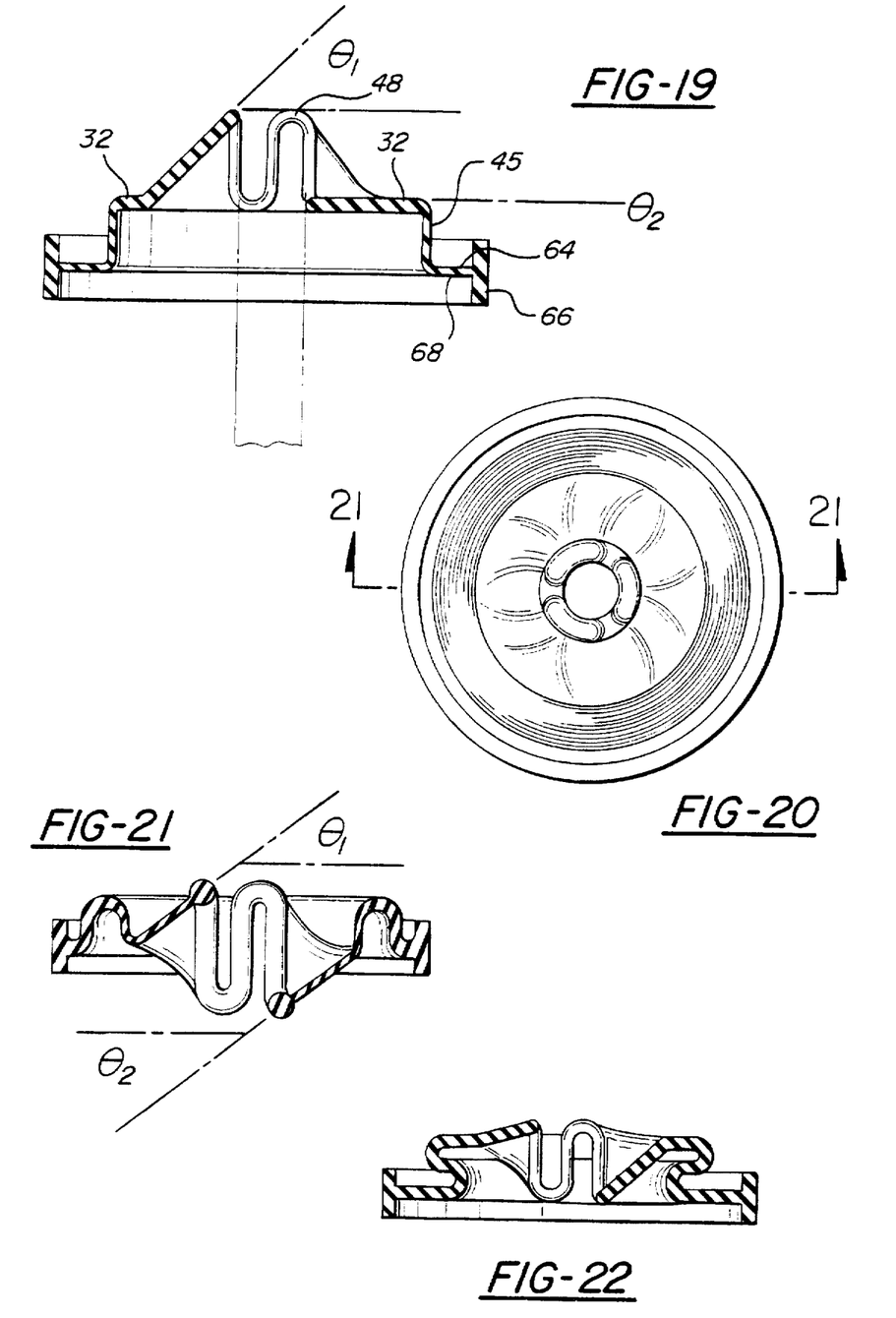
FIG. 19 is a cross-sectional view of an embodiment of the adaptable seal of the present invention having three lobes and a cone-shaped membrane, and having a wall design.
FIG. 20 is a bottom plan view of an embodiment of the adaptable seal of the present invention having three lobes and a prism-shaped membrane.
FIG. 21 is a cross-sectional view taken along line 21—21 in FIG. 20.
FIG. 22 is a cross-sectional view of an embodiment of the adaptable seal of the present invention having three lobes, a prism-shaped membrane, and a horizontal trough.

In one embodiment of the present invention, seal 30 comprises, in its most general form, a membrane having a radially proximal edge, a radially distal edge, and at least one lobe in the membrane terminating at the radially proximal edge, wherein at least a portion of the radially proximal edge defines an adjustable aperture for sealably receiving elongated objects. Preferably, the seal 30 has a band 48 located at the radially proximal edge, wherein the band defines an adjustable aperture for sealably receiving elongated objects. Radially distal circumferential edge 36 may optionally terminate at a trough 54. The trough 54 has an inner circumferential edge 56 and an outer circumferential edge 58. As illustrated in FIG. 3, the trough 54 meets the membrane 32 at the junction of the radially distal circumferential edge 36 of the membrane 32 and the inner circumferential edge 56 of the trough 54. The trough 54 has an inner trough wall 60 and an outer trough wall 62. The outer trough wall 62 defines a groove 64 with inner surface 68 of outer seal wall 66. Where the seal contains no trough, i.e., where the seal is of a wall design, the membrane 32 terminates at wall 45, as illustrated in FIG. 19. In this case, groove 64 is defined by wall 45 and inner surface 68 at outer seal wall 66.

Seal 30 preferably is made from a flexible material, such as rubber or another elastomeric material. The material should be impervious to air and bodily fluids, should have a high tear strength, and should be flexible. The material should not be too stretchable, so that the seal will not be stretched out of shape upon insertion of a surgical instrument. Preferably, the seal is integrally constructed, and is made from a silicone, such as a 50 or 30 durometer shore A liquid silicone rubber. For example, Dow Corning SILASTIC Q7-4850 liquid silicone rubber may be used. Seal 30 may also be made from other silicones, or from materials such as rubber or thermoplastic elastomers. Lubrication may optionally be provided by any suitable lubricant, including fluorosilicone greases and oils. The seal may be impregnated with the lubricant, or, if desired, the seal may also be externally lubricated or lubricated with a surface treatment. Lubrication preferably is provided by coating the surface of the seal with one of the family of PARYLENE compounds available from Specialty Coating Systems, Inc., Indianapolis, Ind. PARYLENE compounds comprise a family of p-xylylene dimers that polymerize when deposited onto a surface to form a hydrophobic polymeric coating. For example, the seals of the present invention may be coated with polymerized dichloro-(2,2)-paracyclophane (PARYLENE C) or di-p-xylylene (PARYLENE N). The PARYLENE monomers are applied to the surface of the seal by gas-phase deposition in a vacuum chamber.

Figures 33, 34, 35:
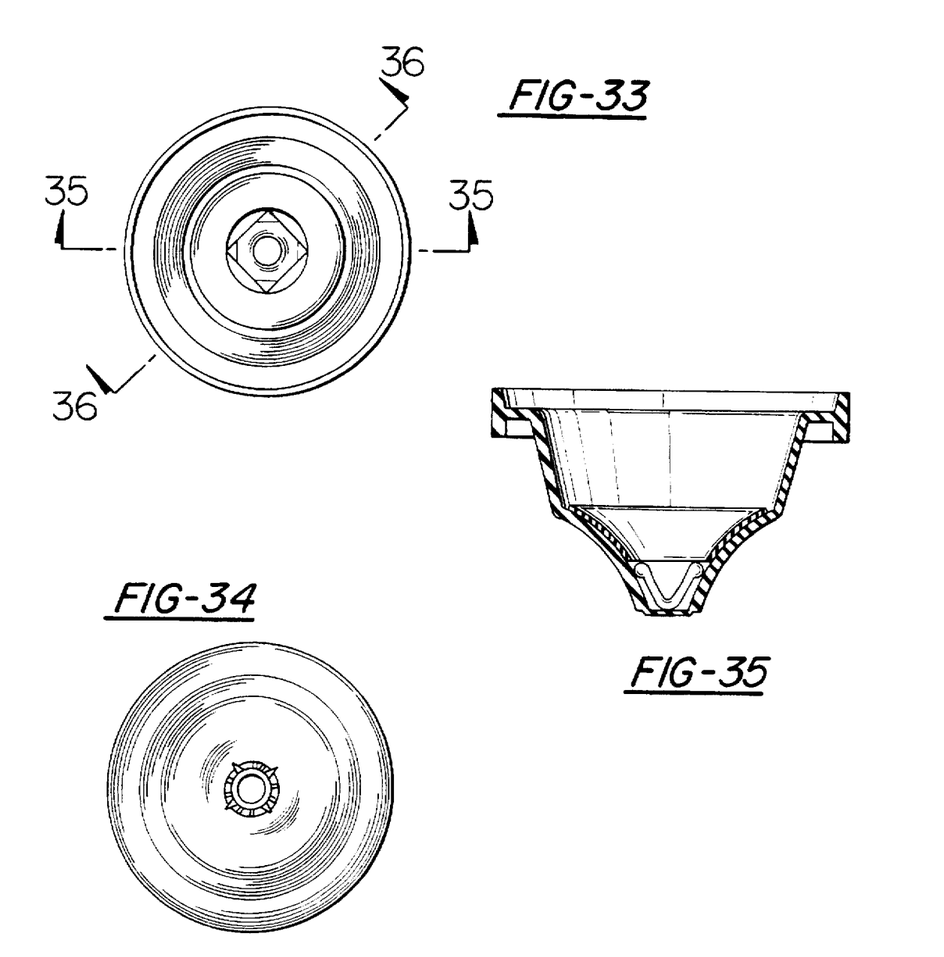
FIG. 33 is a top elevational view of a four-lobed adaptable composite seal having a wall design and a cone-shaped membrane, and including a guide and web.
FIG. 34 is a bottom elevational view of the seal illustrated in FIG. 33.
FIG. 35 is a cross sectional view taken along line 35—35 in FIG. 33.
Figure 36:
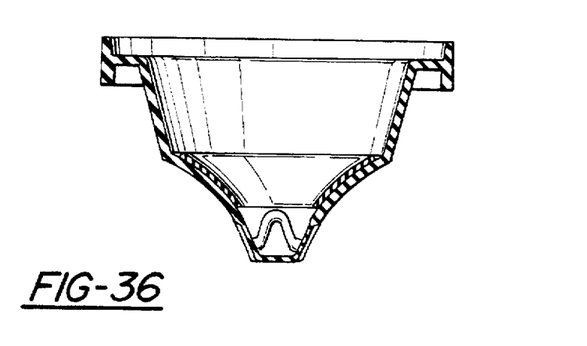
FIG. 36 is a cross sectional view taken along line 36—36 in FIG. 33.

In accordance with a preferred embodiment of the present invention, the adaptable seal is a composite seal 90, as illustrated in FIGS. 33 and 34. The composite seal 90 is in accordance with the seals previously described, and further includes a guide 92 integrally bonded to the upper surface of the membrane 32 below the wall 45 and above the lobes 44, as shown in FIGS. 35 and 36. The guide 92 is added to provide structural support for the composite seal 90, and to provide lubrication for insertion of surgical instruments. Preferably, the guide 92 is bonded to the membrane 32 of the seal after the seal has been fully coated with a PARYLENE.

The guide 92 may be made from any of a number of polymeric materials, including, for example, those selected from the group consisting of ultra-high molecular weight polyethylenes, vinyls, polymerized p-xylylene dimers, and ABS plastics. When the guide 92 is made of a polyethylene, it may be manufactured by vacuum forming, by injection molding, or by hand. When the guide 92 is formed from a polymerized p-xylylene dimer, such as a PARYLENE compound, it can be fashioned by bonding several layers of the compound onto the membrane 32, thus forming an integrally bonded guide.

When the guide 90 is made from polyethylene, as is preferred, it preferably is bonded to the upper surface of the membrane by an acrylic pressure-sensitive adhesive after the seal has been coated with PARYLENE. For example, ultra-high molecular weight polyethylene adhesive-backed tape may be cut by hand and formed into the appropriate shape, i.e., the shape of a truncated cone, then bonded to the membrane 32 of the seal to form a composite seal. Several pieces of such tape may be used, if necessary, to form a guide of the correct shape. Preferably, the guide 92 has a thickness of about 11–12 mils, including 1–2 mils of adhesive (not shown in the Figures). The guide also may be bonded to the membrane by an insert molding process when the seal itself is molded.

The seals of the present invention further preferably include a web 100 bonded to the upper (i.e. inner) surface of the membrane at the lobes 44, as illustrated in FIGS. 33–37. Preferably, the web 100 is integral with the seal, and is molded as a part of the seal at the time the seal is manufactured. The web 100 comprises an elastic cup terminating in an elastic ring 102 for gripping the surgical instruments inserted into the seal and for aiding in the formation of a fluid-tight seal therewith. The web 100 is especially useful for gripping small surgical instruments, when the lobes 44 are unfolded only slightly. In such case, the web 100 insures a fluid-tight grip on the surgical instruments by virtue of the grip of the elastic ring 102.

The seal of the present invention may be made by any number of conventional techniques that are well known to the art. For example, the seal may be molded using liquid injection molding, plastic injection molding, or transfer molding. Preferably, liquid injection molding is used.

Figure 9:
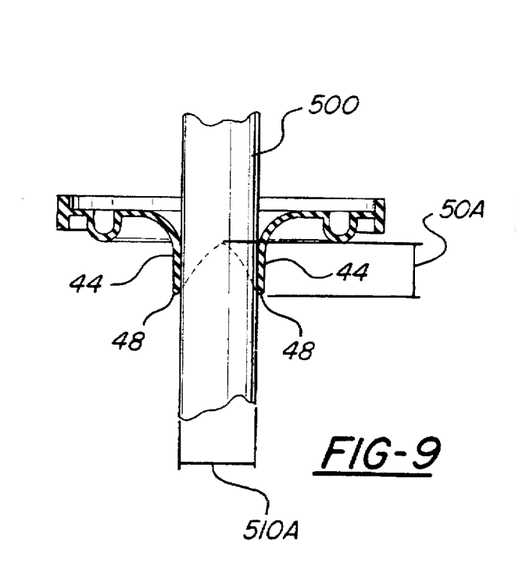
FIG. 9 is a view of the seal illustrated in FIG. 4 taken along line 9—9 illustrating the insertion into the seal of a surgical instrument having a relatively small diameter.
Figure 10:
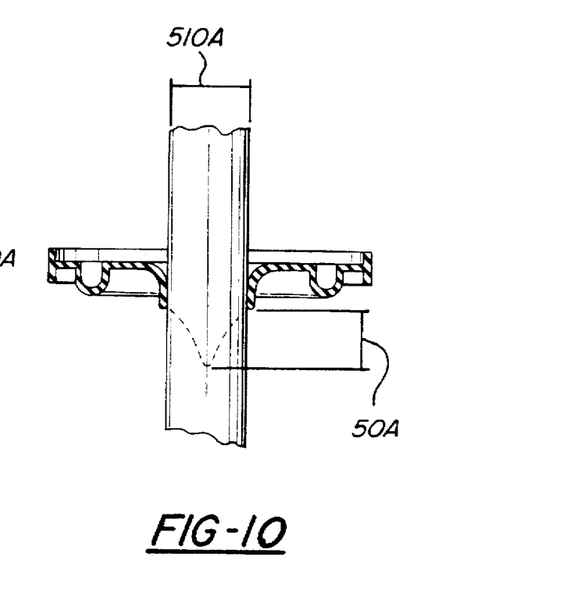
FIG. 10 is a view of the seal illustrated in FIG. 4 taken along line 10—10 illustrating the insertion into the seal of a surgical instrument having a relatively small diameter.

Operation of the seal is illustrated by FIGS. 9, 10, 11, and 12. The seal receives a surgical instrument 500. Surgical instrument 500 has a diameter 510A, in the case of the relatively small surgical instrument illustrated in FIGS. 9 and 10, or diameter 510B, in the case of the relatively large surgical instrument illustrated in FIGS. 11 and 12. With reference to FIGS. 9 and 10, when a relatively small surgical instrument 500 is inserted, lobes 44 will unfold slightly. The expansion of the lobes 44 causes the band 48 to stretch slightly, creating an elastic force around the surgical instrument 500. Thus, a fluid-tight seal around the surgical instrument 500 is effectuated. Because of the unfolding of lobes 44, however, the band 48 stretches only minimally, thus minimizing the drag force on the surgical instrument 500. Stretching of the membrane 32 is minimized by the use of the lobes 44, which unfold to accommodate the elongated surgical instrument.

Figure 11:
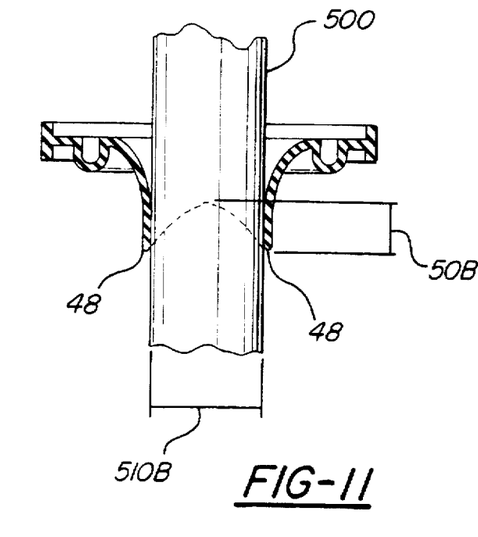
FIG. 11 is a view of the seal illustrated in FIG. 4 taken along line 11—11 illustrating the insertion into the seal of a surgical instrument having a relatively large diameter.
Figure 12:
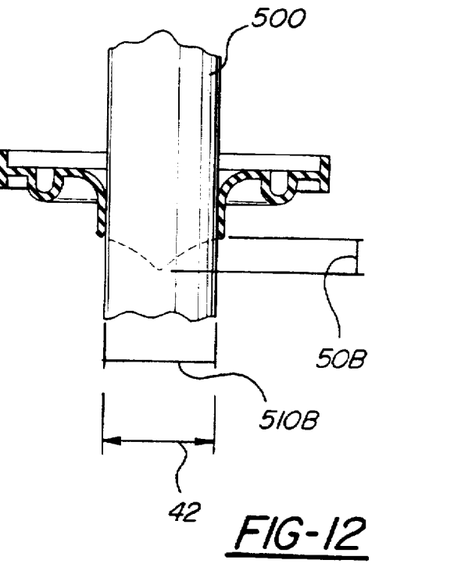
FIG. 12 is a view of the seal illustrated in FIG. 4 taken along line 12—12 illustrating the insertion into the seal of a surgical instrument having a relatively large diameter.

FIGS. 11 and 12 illustrate the operation of the seal with a larger surgical instrument. In this case, lobes 44 unfold to a greater extent than for a smaller surgical instrument. Because band height 50B is smaller than band height 50A, as shown in FIGS. 9–12, the elastic force of band 48 does not greatly increase, but rather is comparable to the elastic force exerted by the band when a smaller surgical instrument engages the seal. This prevents the elastic force from becoming too large, in which case the drag on the surgical instrument would be undesirably high. Band height 50 preferably is 0.220 in. (5.6 mm) when the seal is not in receipt of a surgical instrument.

Figure 6:
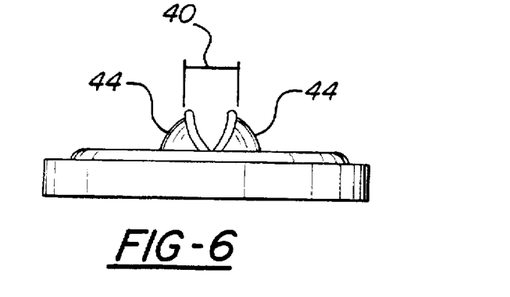
FIG. 6 is a side view of the adaptable seal illustrated in FIG. 1 taken along line 6—6 in FIG. 3.

With reference to FIG. 6, the minimum effective diameter 40 of the aperture 38 should be slightly smaller than the diameter of the shaft of the smallest surgical instrument that the seal is designed to accommodate. Preferably, the minimum effective diameter 40 should be about 75% of the diameter of the surgical instrument. Where, for example, the smallest surgical instrument has a shaft diameter of 5 mm, the minimum effective diameter 40 should be about 3.8 mm. If the minimum effective diameter 40 is so proportioned, the seal will be able to sealably receive the surgical instrument, with a minimum of drag when the instrument is inserted or removed.

With reference to FIG. 12, the maximum unfolded diameter 42 of aperture 38 represents the greatest diameter to which the lobes 44 may unfold without causing the band 48 to stretch significantly. Preferably, the maximum unfolded diameter 42 is about 65% of the maximum diameter of the largest surgical instrument that the seal is designed to accommodate. If the largest surgical instrument has a diameter of 12 mm, for example, the maximum unfolded diameter 42 should be about 0.305 in (7.74 mm). A seal having such dimensions will thus be able to sealably receive the surgical instrument with a minimum of drag when the instrument is inserted or removed.

Figure 25:
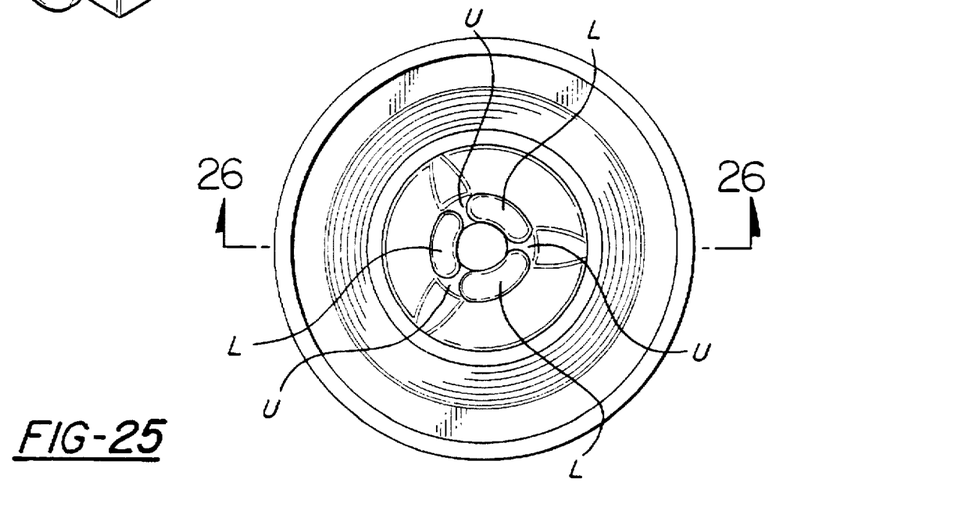
FIG. 25 is a bottom plan view of an adaptable seal having a wall design and a diminished lower-lobe diameter.
Figures 26, 27, 28:
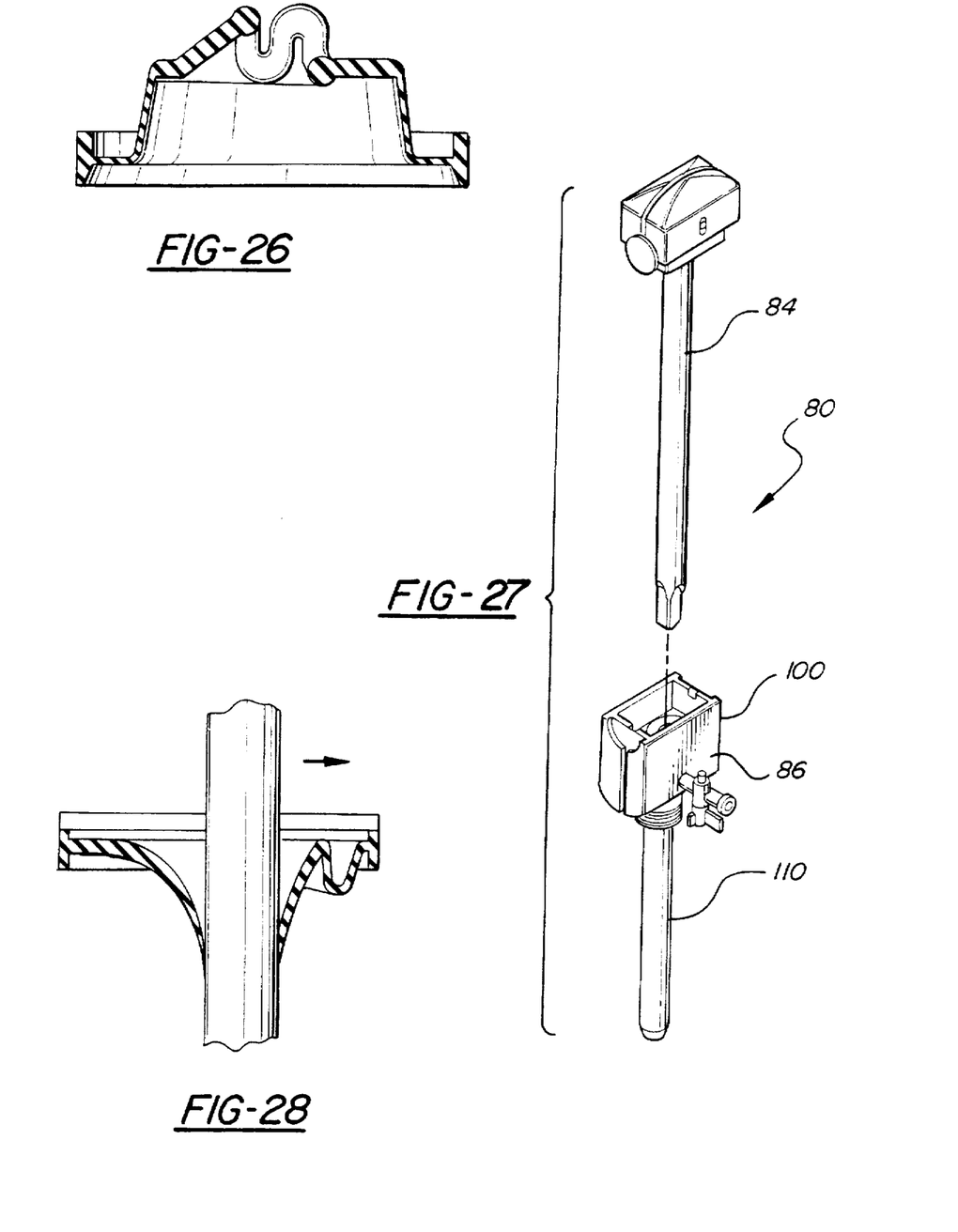
FIG. 26 is a cross-sectional view of the adaptable seal illustrated in FIG. 25.
FIG. 27 is a perspective view of a trocar containing an adaptive seal according to the present invention including an obturator.
FIG. 28 is a cross sectional view of the seal illustrated in FIG. 9 as the surgical instrument moves radially.
Figure 29:
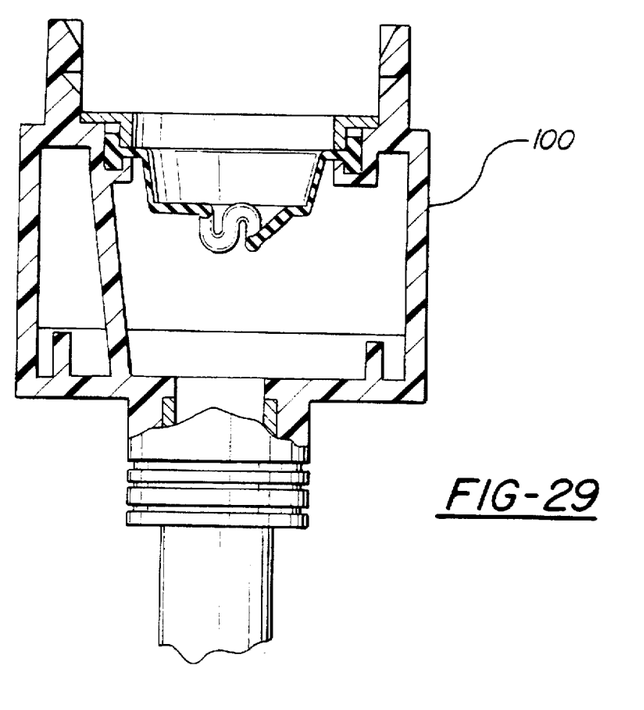
FIG. 29 is a cross-sectional view of a trocar containing an adaptable seal according to the present invention.
Figure 30:
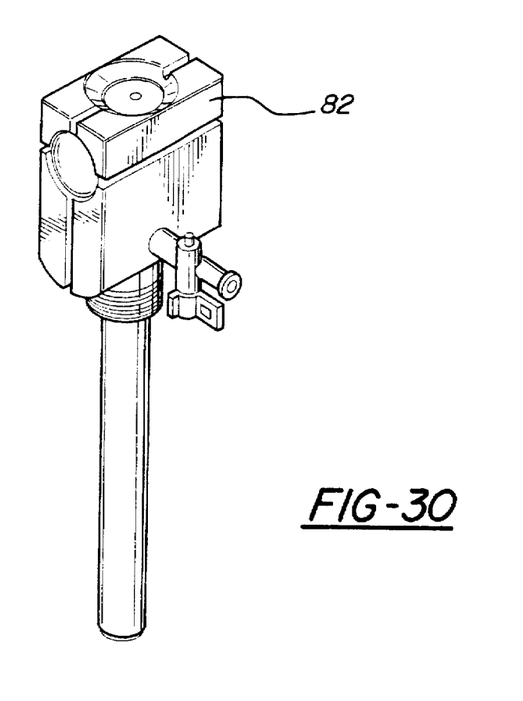
FIG. 30 is a perspective view of a trocar converter according to the present invention as mounted onto a trocar.

In a preferred embodiment, the seal has a lower lobe diameter that is smaller than the upper lobe diameter, as illustrated in FIGS. 25 and 26. Thus, the lower lobe diameter, which is the circle defined by points L in FIG. 25, has a smaller diameter than the upper lobe diameter, which is the circle defined by points U in FIG. 25. When the lower lobe diameter has a smaller diameter than the upper lobe diameter, the gripping force of the seal is maximized at the bottom, or lower lobe diameter. This allows a surgical instrument to be more easily inserted by a surgeon, and assists in radial movement of the surgical instrument within the trocar.

Figure 7:
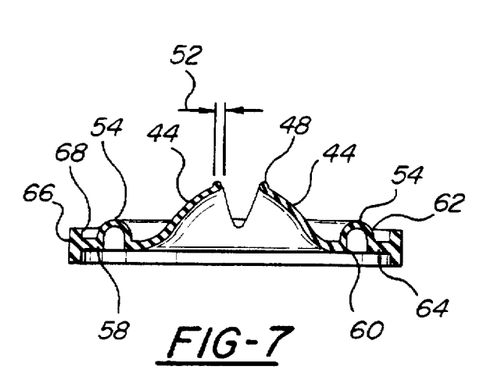
FIG. 7 is a cross-sectional view of the adaptable seal illustrated in FIG. 1 taken along line 7—7 in FIG. 3.
Figure 8:
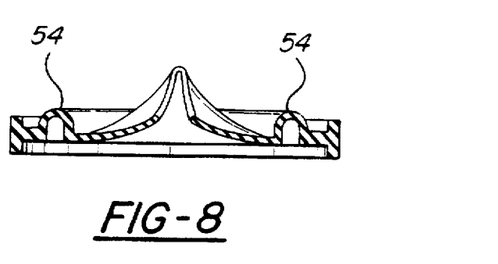
FIG. 8 is a cross-sectional view of the adaptable seal illustrated in FIG. 1 taken along line 8—8 in FIG. 3.

As illustrated in FIG. 3, the band 48 comprises a tube-like belt of material. Band 48 preferably forms a circle when lobes 44 are fully unfolded such that the aperture 38 has a diameter equal to the maximum unfolded diameter 42. Alternatively, the band may form an ellipse or other suitable shape when the lobes 44 are fully unfolded, such as a triangle or square. As illustrated in FIG. 7, band 48 has a band diameter 52. Band diameter 52 may vary from about 0.04 in (1.02 mm) in to about 0.100 in (2.54 mm), and preferably is about 0.08 in (2.03 mm). As the band diameter 52 increases, the tension strength of the band increases. Increasing the tension strength of the band allows for a greater grip around the surgical instrument, but this in turn results in a greater drag force on the instrument when the instrument is inserted or removed. Moreover, the seal 30 is more easily molded when the band diameter 52 is smaller.

Figure 13:
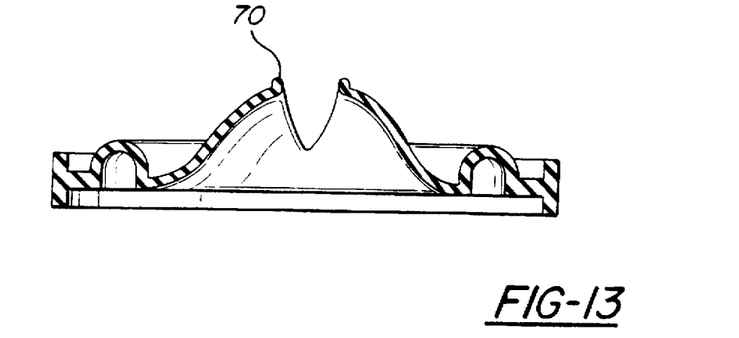
FIG. 13 is a cross-sectional view of an adaptable seal containing a resilient member according to the present invention.

Further, the band 48 may contain a resilient member to increase the tensile strength. As illustrated in FIG. 13, the resilient member preferably comprises a superelastic wire 70. Wire 70 is preferably located within the center of the band 48. When used, wire 70 is preferably made of a superelastic material such as NITINOL, available from Nitinol Devices and Components, Freemont, Calif.

The thickness of membrane 32 may range from about 0.04 in (1 mm) in to about 0.100 in (2.54 mm). The thinner membranes assist in reducing the drag force on the surgical instrument. However, if the membrane is made too thin, the seal may invert upon removal of the surgical instrument, possibly causing a disruption in the fluid-tight seal around the surgical instrument. As the membrane is made thicker with respect to the thickness of the wall 45 or trough 54, the seal is better able to accommodate radial movement. Similarly, increasing the band diameter renders the seal more able to accommodate radial movement. When the band diameter 52 is 0.08 in (2.03 mm), the membrane preferably has a thickness of 0.07 in (1.78 mm). The thickness of the membrane is preferably constant between the radially proximal circumferential edge 34 and the radially distal circumferential edge 36. However, the thickness of the membrane may vary. For example, the thickness may taper towards or away from the radially proximal circumferential edge 34.

Figure 14:
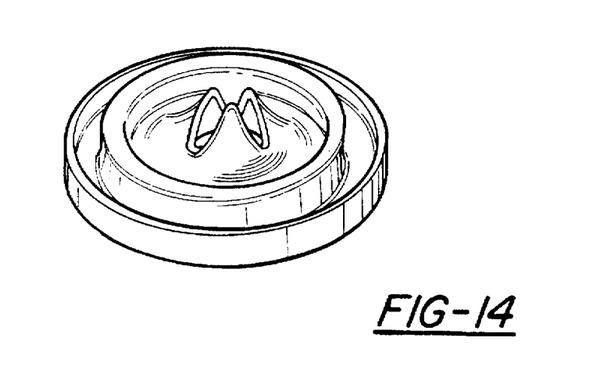
FIG. 14 is a bottom perspective view of an embodiment of the adaptable seal of the present invention having three lobes and a cone-shaped membrane.
Figures 15, 16:
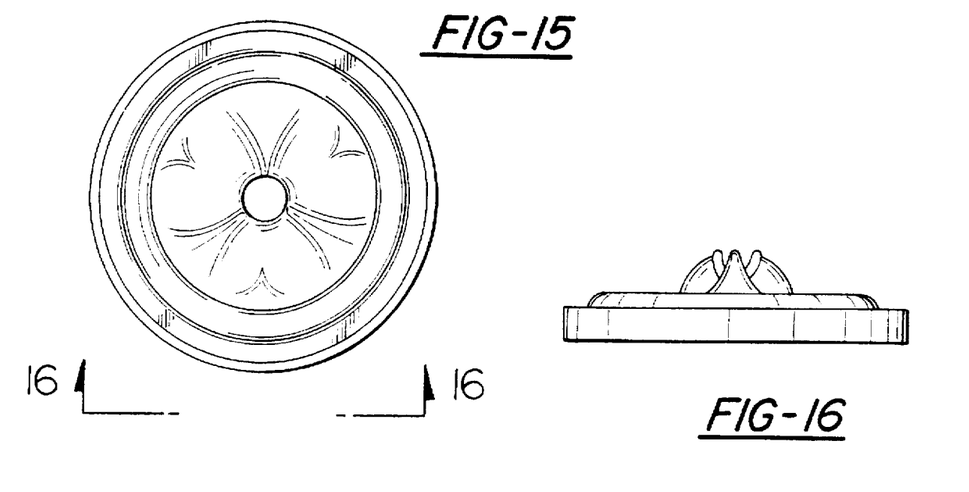
FIG. 15 is a bottom plan view of the adaptable seal illustrated in FIG. 14.
FIG. 16 is a side view taken along line 16—16 in FIG. 15.

The membrane 32 contains one or more lobes 44. Preferably, membrane 32 contains four lobes, as illustrated in FIGS. 33 and 34. The membrane 32 may also contain three lobes, as illustrated in FIGS. 14–16. Alternatively, the membrane 32 may contain a different number of lobes. For example, as illustrated in FIGS. 1–13, the membrane may contain two lobes. As the number of lobes increases, the gripping force on smaller surgical instruments increases, and the seal becomes more likely to remain intact upon radial movement of the surgical instrument. However, the seal becomes more difficult to mold as the number of lobes increases.

Membrane 32 may have any suitable shape. FIGS. 19 and 21 illustrate cone-shaped and prism-shaped membranes respectively. The membrane shape may be defined by the angles formed by lines parallel to the upper- and lower-most portions of the membrane and the plane of the seal, designated as $\theta_1$, and $\theta_2$ in FIGS. 19 and 21. Angles $\theta_1$ and $\theta_2$ may range from 0° to approximately 60°, preferably from 0° to 45°. When either one of the angles $\theta_1$, $\theta_2$ is zero, the membrane is cone-shaped, as illustrated in FIG. 19. When $\theta_1=\theta_2$, the membrane is prism-shaped, as illustrated in FIG. 21. Angles $\theta_1$ and $\theta_2$ may by similarly defined for embodiments having a different number of lobes than shown in FIGS. 19 and 21. If the band 48 in FIG. 19 were displaced in the direction of the arrow, with a corresponding displacement of the membrane, the membrane shape shown in FIG. 21 would result. Of course, the combination of angles $\theta_1$ and $\theta_2$ are not limited to the prism-shaped and cone-shaped embodiments illustrated in FIGS. 21 and 19. Indeed, $\theta_1$ and $\theta_2$ may independently have any suitable values.

Figure 37:
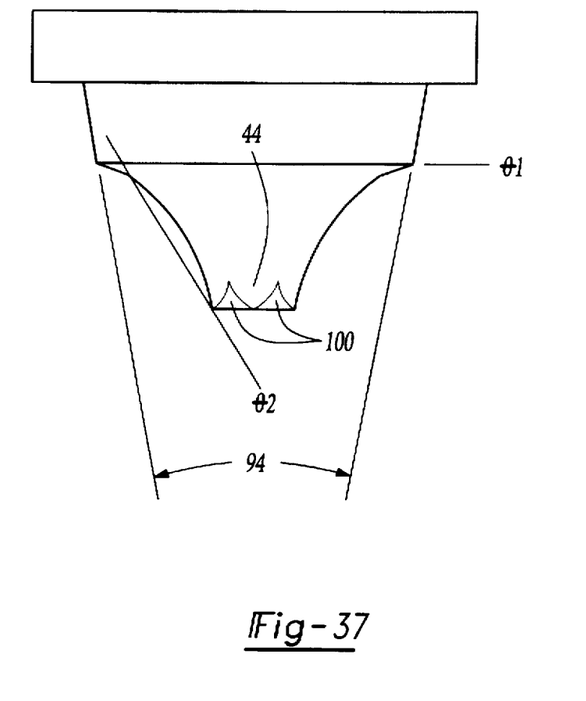
FIG. 37 is a side elevational view of the seal illustrated in FIG. 33.

The shape of the lobes is funnel-like, and thus assists in guiding the surgical instrument into the cannula. When the membrane is cone-shaped, the funnelling effect of lobes is maximized. When the membrane is prism-shaped, the seal integrity around the surgical instrument as the surgical instrument moves radially is greater than as compared to the cone-shaped design. Either design is useful in the adaptable seal of the present invention. Preferably, the seal is cone shaped, having a slightly bowed cross section with $\theta_1 = 45°$. FIGS. 35–37 illustrate the preferred shape of the membrane in the four-lobed preferred embodiment of the seal. FIG. 37 illustrates the definition of $\theta_1$ and $\theta_2$ in this embodiment.

Figure 32:
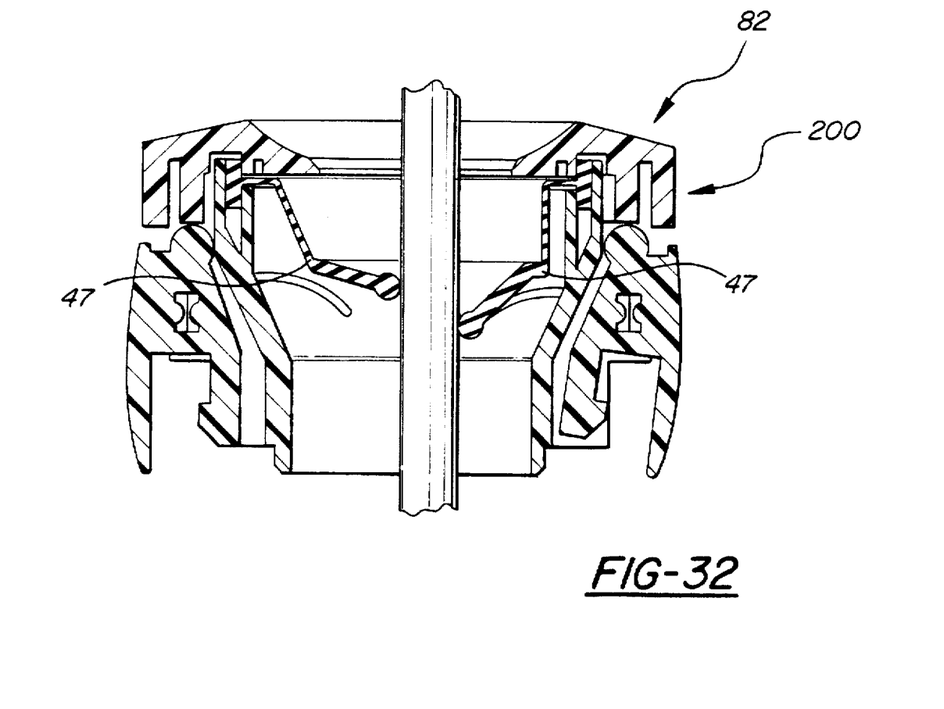
FIG. 32 is a partial cross sectional view of the trocar converter shown in FIG. 23, illustrating radial movement of a surgical instrument.

The seal of the present invention may be designed with or without a trough. When the seal is designed without a trough, the wall angle 94, as defined in FIG. 37, preferably is 30°. When a trough is used, the material thickness of the trough preferably ranges from 0.005 in (0.13 mm) to 0.05 in (1.29 mm), and is preferably 0.015 in (0.38 mm). Where a wall design is used without a trough, the wall 45 has a similar range of thicknesses, and preferably has a thickness of 0.015 in (0.38 mm). A seal according to the wall design allows for radial movement of the surgical instrument by virtue of the relative thickness of the membrane and wall. Preferably, as illustrated in the seal shown in FIGS. 23 and 32, the membrane 32 is relatively thick as compared to the wall 45. As the surgical instrument is moved radially, one or more of bends 47 flexes, as illustrated in FIG. 32. As the vertical height of the wall increases, radial movement is facilitated. Similarly, as the wall becomes thinner, radial movement is facilitated. The wall must not be made too thin, however, as this may cause the seal to stretch, rupture, or invert upon removal of the surgical instrument.

Figure 31:
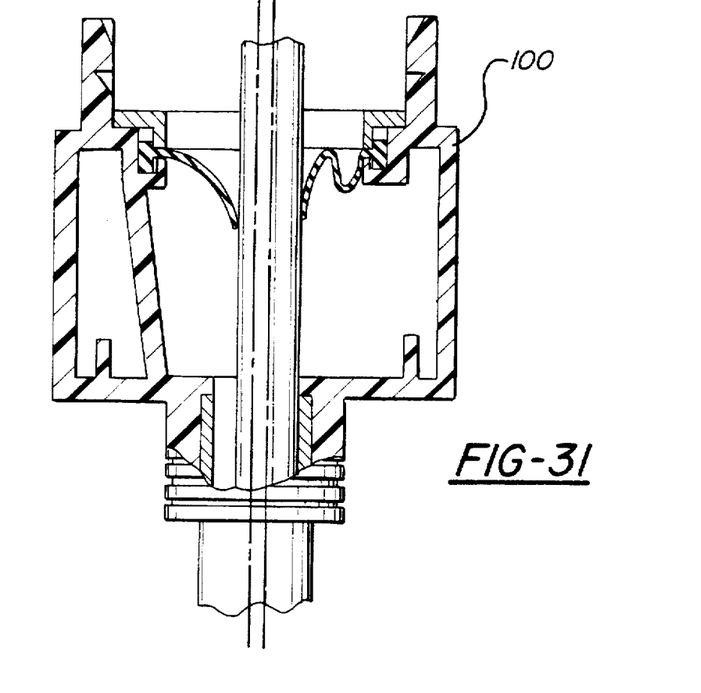
FIG. 31 is a cross-sectional view of a trocar containing a seal having a trough, and including a surgical instrument illustrating radial movement of the surgical instrument.

When a trough is used, the trough 54 meets the membrane 32 at the radially distal circumferential edge 36 of the trough, as shown in FIG. 4. Trough 54 is adapted to accommodate radial movement of the surgical instrument. The trough unfolds when the surgical instrument moves radially within the trocar as illustrated in FIGS. 28 and 31. As in the case of the wall design, as the trough is made thinner, radial movement of a surgical instrument is facilitated. Of course, if the trough is made too thin, rupture or other undesirable effects may occur. Because the trough and wall are annular, the seal is able to accommodate radial movement of the surgical instrument in any direction.

Figure 17:
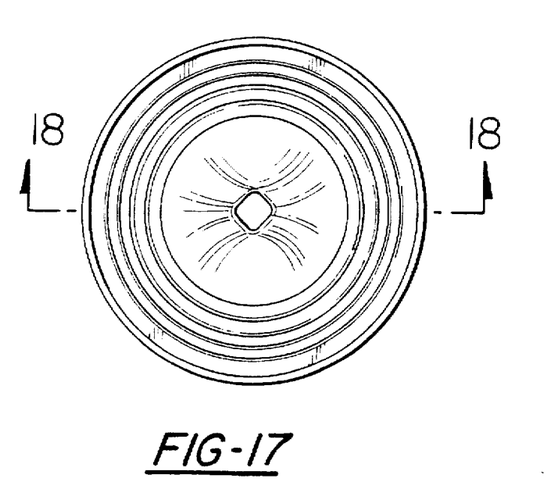
FIG. 17 is a bottom plan view of an embodiment of the adaptable seal of the present invention having a plurality of troughs.
Figure 18:
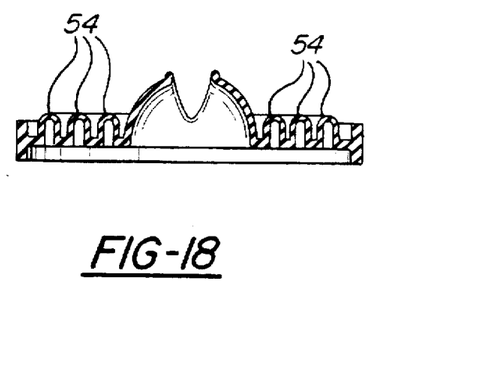
FIG. 18 is a cross-sectional view taken along line 18—18 in FIG. 17.

The trough 54 may be of any suitable shape. When used, the trough preferably is vertical, i.e., it has a generally U-shaped cross-section, as illustrated in FIGS. 9–12. The trough may also be horizontal, i.e., it may also have a generally S-shaped cross section as illustrated in FIG. 22. The trough may have any other suitable shape, and any number of horizontal or vertical troughs may be included with the seal of the present invention. For example, two or more troughs can be provided. FIGS. 17 and 18 illustrate a three-troughed embodiment of the adaptable seal of the present invention. As the number of troughs increases, the height of each trough may decrease without sacrificing the ability to accommodate radial motion of the surgical instrument.

The outer circumferential edge 58 of trough 54 preferably meets a groove 64, as illustrated in FIG. 7. Groove 64 is the surface adjacent to the inner surface 68. The groove 64 preferably is defined by outer trough wall 62 and inner surface 68 of outer seal wall 66. Where the seal contains a plurality of troughs, the groove 64 is defined by the outer trough wall of the outermost trough, i.e., the trough that is radially the farthest from the center of the seal. Where the seal contains a wall and does not contain a trough, the groove 64 is defined by wall 45 and inner surface 68 of outer seal wall 66, as illustrated in FIG. 19.

Figure 24:
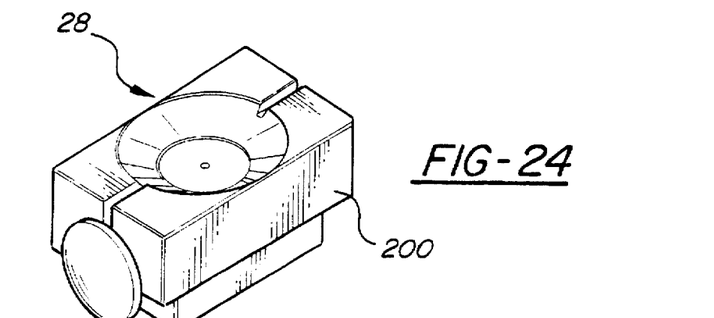
FIG. 24 is a perspective view of a trocar converter containing the adaptable seal illustrated in FIG. 14.

Groove 64 has dimensions such that it may be used to retain the seal of the present invention in a trocar 80 or trocar converter 82, as illustrated in FIGS. 27 and 24 respectively. Preferably, the seal is held in place within the trocar 80 or trocar converter 82 by pressure between upper and lower halves of the housing of the trocar or trocar converter. For example, the upper half of the housing may include a ring (not shown) designed to fit within the groove. When the trocar or trocar converter is assembled, the ring fits within the groove and presses against the lower half of the housing, thereby securing the seal within the housing.

In another general embodiment of a seal according to the present invention, the seal includes a membrane having an aperture for forming a fluid-tight seal between upper and lower surfaces of the seal and at least one trough located at the radially distal edge of the seal. A seal according to this embodiment of the present invention may but need not include the band-and-lobe arrangement previously set forth. Any design may be used for the trough; for example, the trough may be horizontal or vertical. In addition, a plurality of troughs may be employed. A seal according to this general embodiment of the present invention is able to accommodate radial movement of a surgical instrument.

In yet another general embodiment of a seal according to the present invention, the seal includes a membrane having an aperture for forming a fluid-tight seal between upper and lower surfaces of the seal and at least one wall located at the radially distal edge of the seal. A seal according to this embodiment of the present invention may but need not include the band-and-lobe arrangement previously set forth. A seal according to this general embodiment of the present invention is able to accommodate radial movement of a surgical instrument. Preferably, the material thickness of the wall is less than the material thickness of the membrane.

Figure 23:
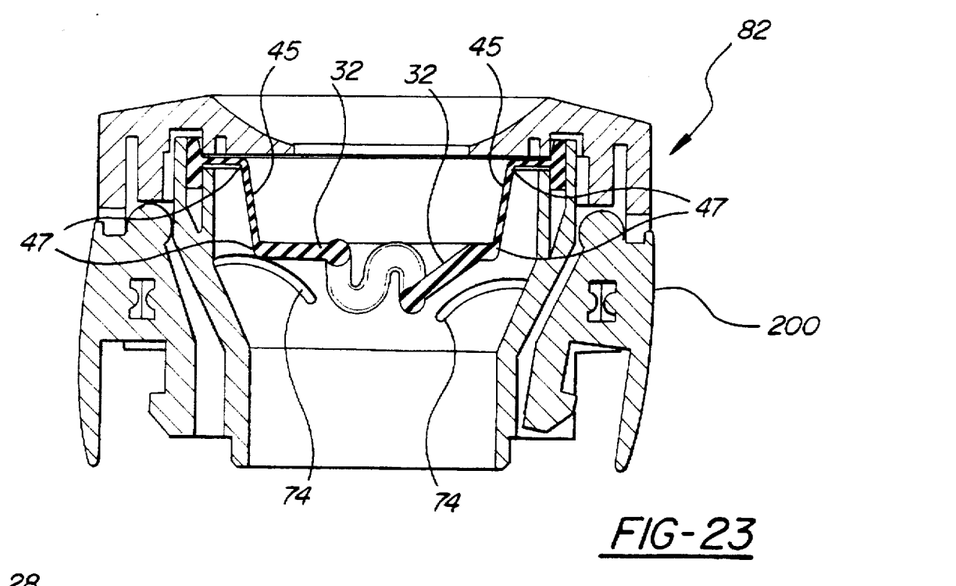
FIG. 23 is a cross sectional view of a trocar converter containing the seal illustrated in FIG. 14.

A trocar converter 82 and a trocar 80, as illustrated in FIGS. 27 and 24 respectively, also fall within the purview of the present invention. In its most general form, a trocar according to the present invention comprises an obturator 84 and a cannula 86. The cannula 86 includes a housing 100, a tube 110 extending from the housing, and a seal secured to the housing to sealably receive elongated surgical instruments. The seal used in the trocar is a seal according to the present invention. When an adaptable seal of the present invention is used in a trocar, the trocar may replace a wide variety of trocars and converters, thus eliminating the time needed to organize, store, and retrieve trocars and converters of different sizes. Similarly, a trocar converter 82 according to the present invention comprises a housing 200 and an seal secured to the housing, as illustrated in FIGS. 23 and 24. The seal is a seal as disclosed herein.

When a seal according to the present invention is mounted in a trocar or trocar converter, one or more springs 74 may be included within the housing 100, as illustrated in FIG. 23 with respect to a trocar converter. The springs 74 increase the grip of the seal on the surgical instrument. Any suitable resilient material may be used to construct springs 74.

When an adaptable seal of the present invention is mounted in a trocar 80, the trocar 80 must be able to sealably close off the cannula when a surgical instrument is not present within the cannula. Accordingly, the seal of the present invention may be used in conjunction with a slit seal of the type commonly known in the art (not shown). Alternatively, or in addition thereto, the seal may be used in conjunction with a spring-loaded sealing flap that operates to secure the cannula when the surgical instrument is removed (not shown). Further, the adaptable seal of the present invention itself may be modified so that it provides an adequate seal for the cannula when no surgical instrument is present within the trocar.

The seals of the present invention thus overcome the drawbacks of conventional seals. A surgeon may use surgical instruments having a variety of diameters using a single trocar or trocar converter. In addition, the use of a seal according to the present invention allows for radial movement of the surgical instrument within the trocar. Further, the seal of the present invention is very simple in design and inexpensive to manufacture. Moreover, a seal according to the present invention does not require a complex mechanism in order to sealably receive surgical instruments of various diameters. Trocars and trocar converters according to the present invention share similar advantages.

While particular embodiments of the invention have been shown, it will of course be understood that the invention in not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

What is claimed is:

1. An adaptable seal for sealably receiving elongated surgical objects of various diameters, said adaptable seal comprising:
   a membrane, said membrane having an aperture adapted to receive said elongated surgical object, said aperture being defined by a perimeter edge having a normal non-sealing position when said surgical instrument is absent and a sealing position against said surgical instrument when said surgical instrument is present, and
   at least one lobe in said membrane, said lobe originating at said aperture providing accumulated material allowing said perimeter edge to expand as said surgical instrument is inserted without stretching the perimeter edge;
   wherein said band defines an adjustable aperture which expands for various sizes of surgical instruments without excessive friction against said instrument for receiving said elongated objects without undue frictional contact.

2. An adaptable seal according to claim 1, including a plurality of lobes.

3. An adaptable seal according to claim 1, including two lobes.

4. An adaptable seal according to claim 1, including three lobes.

5. An adaptable seal according to claim 1, wherein said seal has an outer edge and at least one trough located adjacent said outer edge.

6. An adaptable seal according to claim 5, wherein said trough is a horizontal trough.

7. An adaptable seal according to claim 5, wherein said trough is a vertical trough.

8. An adaptable seal according to claim 5, including at least two lobes.

9. An adaptable seal according to claim 5, including at least three lobes.

10. An adaptable seal according to claim 5, including a plurality of troughs located at said outer edge.

11. An adaptable seal according to claim 1, wherein said membrane is prism-shaped.

12. An adaptable seal according to claim 1, wherein said membrane is cone-shaped.

13. A seal according to claim 1, wherein said seal has a lower lobe diameter and an upper lobe diameter, wherein said lower lobe diameter is smaller than said upper lobe diameter.

14. An adaptable seal according to claim 1, further including a band located about said perimeter edge.

15. An adaptable seal according to claim 14, wherein said band contains a resilient member.

16. An adaptable seal according to claim 15, wherein said resilient member is a wire.

17. A trocar converter comprising:
   a housing; and
   an adaptable seal secured to said housing; wherein said adaptable seal comprises the adaptable seal of claim 1.

18. A trocar converter according to claim 17, wherein said adaptable seal further comprises at least one trough located at said radially distal edge.

19. A trocar comprising:
   a housing;
   a cannula extending from said housing; and
   an adaptable seal secured to said housing, wherein said adaptable seal is the adaptable seal of claim 1.

20. An adaptable seal according to claim 1, including four lobes.

21. An adaptable seal according to claim 1, said membrane having an upper surface, said seal including a guide integrally bonded to said upper surface of said membrane.

22. An adaptable seal according to claim 21, wherein said guide comprises a polymeric material selected from the group consisting of ultra-high molecular weight polyethylenes, vinyls, polymerized p-xylylene dimers, and ABS plastics.

23. An adaptable seal according to claim 22, wherein said guide comprises ultra-high molecular weight polyethylene.

24. An adaptable seal according to claim 21, wherein said guide is composed of a polymerized p-xylylene dimer.

25. An adaptable seal according to claim 1, said seal including a web bonded to the upper surface of the membrane at the lobes.

26. An expandable seal for sealably receiving elongated surgical instruments of various diameters, said expandable seal comprising:
   a membrane having an aperture defined by an edge of the membrane surrounding the aperture, said aperture being expandable between a first diameter and a second larger diameter said first diameter being a normal non-sealing position when said surgical instrument is absent and said second diameter being a sealing position to seal against said surgical instrument when said surgical instrument is present;
   said edge being folded with respect to itself to engage said instrument along the length of said edge as said instrument is inserted, said edge unfolding to said second larger diameter while engaging said instrument to expand said aperture as said instrument is inserted.

27. A trocar converter comprising:
   a housing; and
   a seal secured to said housing;
   wherein said seal comprises the seal of claim 26.

28. A trocar converter according to claim 27, wherein said seal includes at least one lobe.

29. The seal according to claim 26, further including a trough.

30. A trocar comprising:

a housing;

a cannula extending from said housing; and a seal secured to said housing;

wherein said seal is the seal of claim 29.

31. A trocar according to claim 30, wherein said seal includes at least one lobe.

32. The seal of claim 29, wherein said trough is a horizontal trough.

33. A seal according to claim 29, wherein said trough is a vertical trough.

34. A seal according to claim 29 further comprising a plurality of troughs.

* * * * *